United States Patent
Nagai et al.

(10) Patent No.: US 6,322,506 B1
(45) Date of Patent: Nov. 27, 2001

(54) INCLINATION ANGLE DETECTING DEVICE FOR AN ULTRASOUND PROBE

(75) Inventors: Hiroshi Nagai, Tokyo; Kohei Ono, Higashiyamato; Eishi Harasawa, Iruma, all of (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/354,120

(22) Filed: Jul. 15, 1999

(30) Foreign Application Priority Data

Jul. 16, 1998 (JP) .................................................. 10-201678

(51) Int. Cl.[7] .................................................. A61B 8/00
(52) U.S. Cl. ........................................... 600/437; 600/459
(58) Field of Search ..................... 600/437, 441, 600/443, 447, 459; 128/916; 73/624, 623, 625, 629, 626; 367/7, 11

(56) References Cited

U.S. PATENT DOCUMENTS

| 4,570,488 | * | 2/1986 | Miwa et al. | 73/626 |
| 5,152,294 | * | 10/1992 | Mochizuki et al. | 600/459 |
| 5,329,929 | * | 7/1994 | Sato et al. | 600/441 |
| 5,682,895 | * | 11/1997 | Ishiguro | 600/440 |

* cited by examiner

Primary Examiner—Marvin M. Lateef
Assistant Examiner—Ali M. Imam
(74) Attorney, Agent, or Firm—Hoffmann & Baron, LLP

(57) ABSTRACT

An inclination angle detecting device comprises a reference arm attached near the contact area of an ultrasound probe with one end thereof being rotatably attached, a pressing means which presses the reference arm in a direction away from the ultrasound probe, and a detecting unit for detecting the amount of rotation of the reference arm. Placing the ultrasound probe against the surface of the body causes the reference arm to be rotated and pressed against the surface of the body in close contact, whereby the inclination angle is detected from the amount of rotation.

3 Claims, 7 Drawing Sheets

INCLINATION ANGLE DETECTING DEVICE FOR AN ULTRASOUND PROBE

BACKGROUND OF THE INVENTION

1. Field of the Invention

The present invention relates to an apparatus for obtaining three-dimensional area images within a physiological body with an ultrasound apparatus, and creating three-dimensional images.

2. Description of the Related Art

Medical ultrasound apparatuses are used for visualizing cross-sections of internal organs or disease tissue from data obtained by an ultrasound probe. Conventional arrangements for such apparatuses involve an operator moving or inclining the ultrasound probe in an arbitrary manner to record multiple sets of cross-section data, thereby creating three-dimensional images of the object of measurement. However. the position and angle of the ultrasound probe cannot be precisely obtained with such an apparatus, so precise three-dimensional images could not be created.

On the other hand, there is a method wherein the ultrasound probe is attached to an arm supported on the outside of the subject. thereby obtaining reference coordinates on the outside of the subject and obtaining the position and inclination angle of the ultrasound probe based on the movement of the arm from the coordinates, so as to obtain a three-dimensional image (Japanese Unexamined Patent Publication No. 2-172452). However, such an apparatus is complicated in structure. and is als problematic in that the subject cannot move during the measurement.

In other words, conventional apparatuses have been defective in that attempts to easily obtain three-dimensional images results in loss of precision, and attempts to obtain precise three-dimensional images results in a complex apparatus, which is burdensome for the subject.

SUMMARY OF THE INVENTION

Accordingly, it is an object of the present invention to provide an apparatus which is simple in structure, easy to operate, does not place a great burden on the subject, and al lows precise three-dimensional images to be obtained.

To this end, the present invention comprises an inclination angle detecting device for an ultrasound probe, the inclination angle detecting device comprising: a reference arm attached near the contact area of the ultrasound probe with one end thereof being rotatably attached; a detecting unit for detecting the inclination angle of the ultrasound probe as to the reference arm; and further preferably a first pressing means which presses the reference arm in a direction away from the ultrasound probe in a rotating manner.

Accordingly, pressing the contact area of the ultrasound probe against the surface of the body of the subject in contact of the reference arm with the skin-surface of the body of the subject the detecting unit detects the inclination angle. This apparatus is simple in structure, easy to operate, does not place a great burden on the subject, and allows precise three-dimensional images to be obtained. By means of first pressing means, pressing the contact area of the ultrasound probe against the surface of the body of the subject brings the reference arm into close contact with the skin-surface of the body of the subject. In the event that the operator tilts the ultrasound probe while the reference arm is in close contact with the surface of the body of the subject. The detecting unit detects the inclination angle further precisely.

Further, even more precise three-dimensional images can be obtained by an arrangement wherein the inclination angle detecting device further comprises: a slide portion slidably provided along the side of the ultrasound probe; and a second pressing means which presses the slide portion in a direction toward the contact area of the ultrasound probe and beyond; wherein one end of the reference arm is rotatably attached at the tip of the slide portion. That is to say, regardless of how the operator tilts the ultrasound probe while the ultrasound probe is in close contact with the surface of the body of the subject, the slide portion slides, and the tip is always at the same position on the surface of the body of the subject. Accordingly, the reference arm is always in close contact with the surface of the body of the subject.

DETAILED DESCRIPTION OF THE PREFERRED EMBODIMENTS

Figure 1:
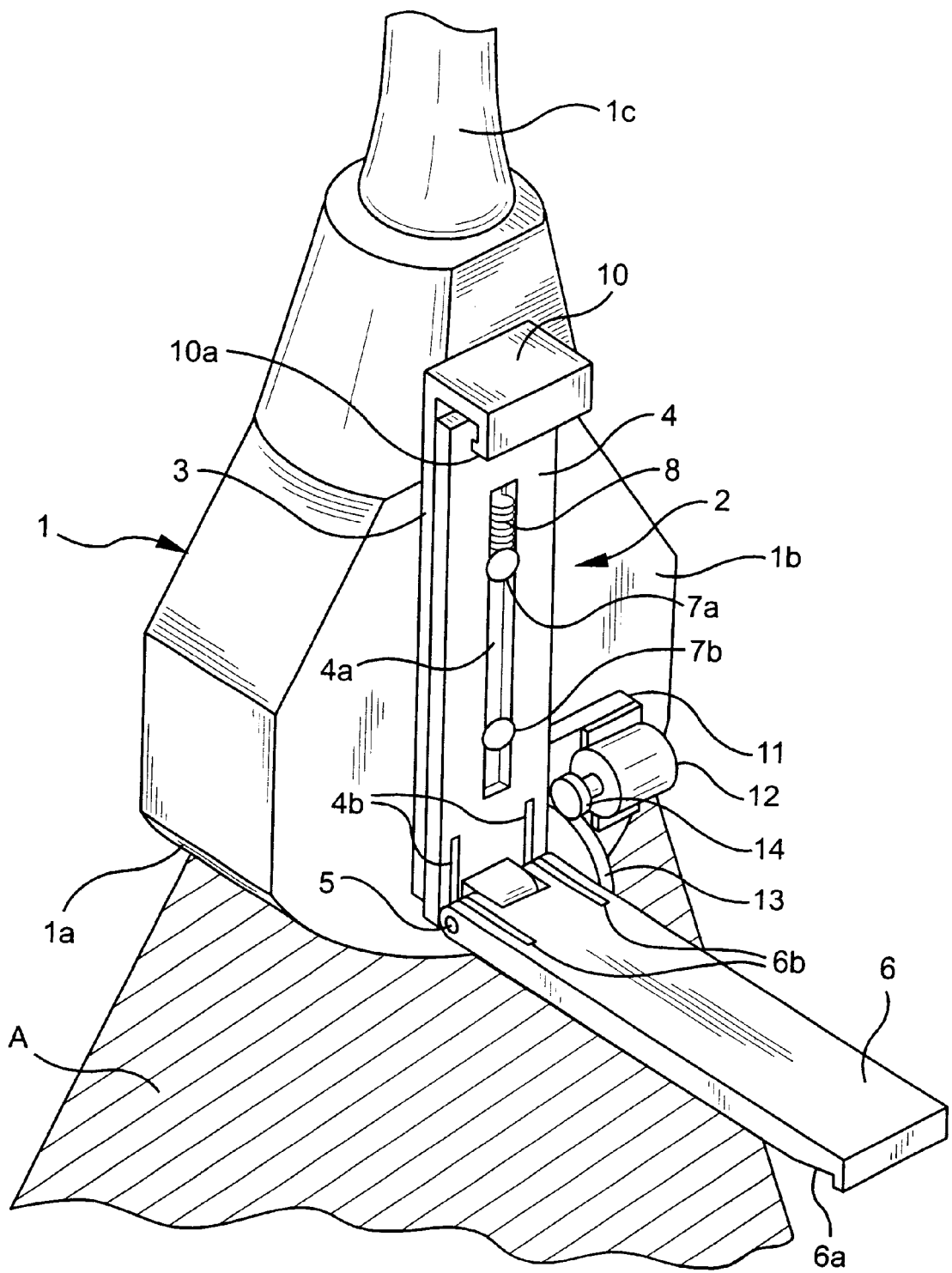
FIG. 1 is a perspective view illustrating the ultrasound probe with an inclination angle detecting device according to the present invention.

FIG. 1 is a perspective view of an embodiment of the present invention. As shown in the Figure, the inclination angle detecting device 2 is attached to the ultrasound probe 1. The ultrasound probe 1 is a array probe wherein a plurality of ultrasound transducers are arrayed in single file, and the scanning plane (tomography) thereof is a plane orthogonal with the tip plane. namely contact area 1a which sends and receives ultrasound, as shown by A in the Figure.

The inclination angle detecting device 2 has a base plate 3 provided to the side plane 1b of the ultrasound probe 1, a slide plate 4 slidably provided to this base plate 3 so as to serve as the slide portion. a shaft 5 rotatably provided to one end of this slide plate 4, and a reference arm 6 provided to one end of this shaft 5 that allows the reference arm 6 to rotate in fan-like sweeping manner.

Figure 2:
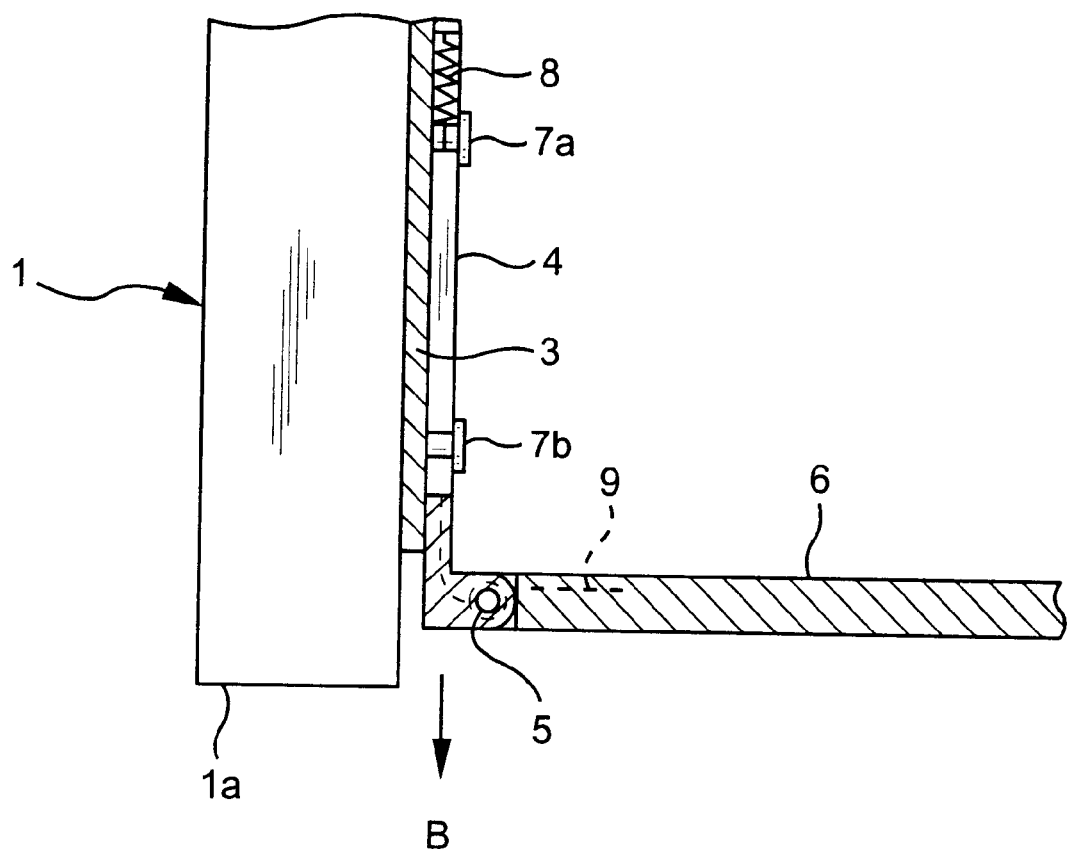
FIG. 2 is a cross-sectional view of the principal portions of the inclination angle detecting device shown in FIG. 1.

A slit 4a is provided in the longitudinal direction of the slide plate 4. A pair of pins 7a and 7b erected on the base plate 3 are inserted through the slit 4a. The diameter of the head portion of the pins 7a and 7b is greater than the width of the slit 4a. The slide plate is prevented from separating from the base plate 3 by the pins 7a and 7b. On the other hand, a cylindrical coil spring 8 is provided between pin 7a and one end of the slit 4a of the slide plate 4. serving as second pressing means. A shown by the arrow B in the cross-section diagram in FIG. 2, this cylindrical coil spring 8 presses the slide plate 4 so that the tip thereof reaches the direction of the contact are 1a of the ultrasound probe 1, and further protrudes beyond the contact are 1a.

Further, between the slide plate 4 and reference arm 6, a pair of torsion coil springs 9 are wrapped around the shaft 5 so as to serve as a first pressing means. The torsion coil springs 9 are for pressing so that the angle between the slide plate 4 and the reference arm 6 is around 180°. The torsion coil springs 9 are stored in grooves 4b and 6b(see FIG. 1) provided in the slide plate 4 and reference arm 6.

Figure 3:
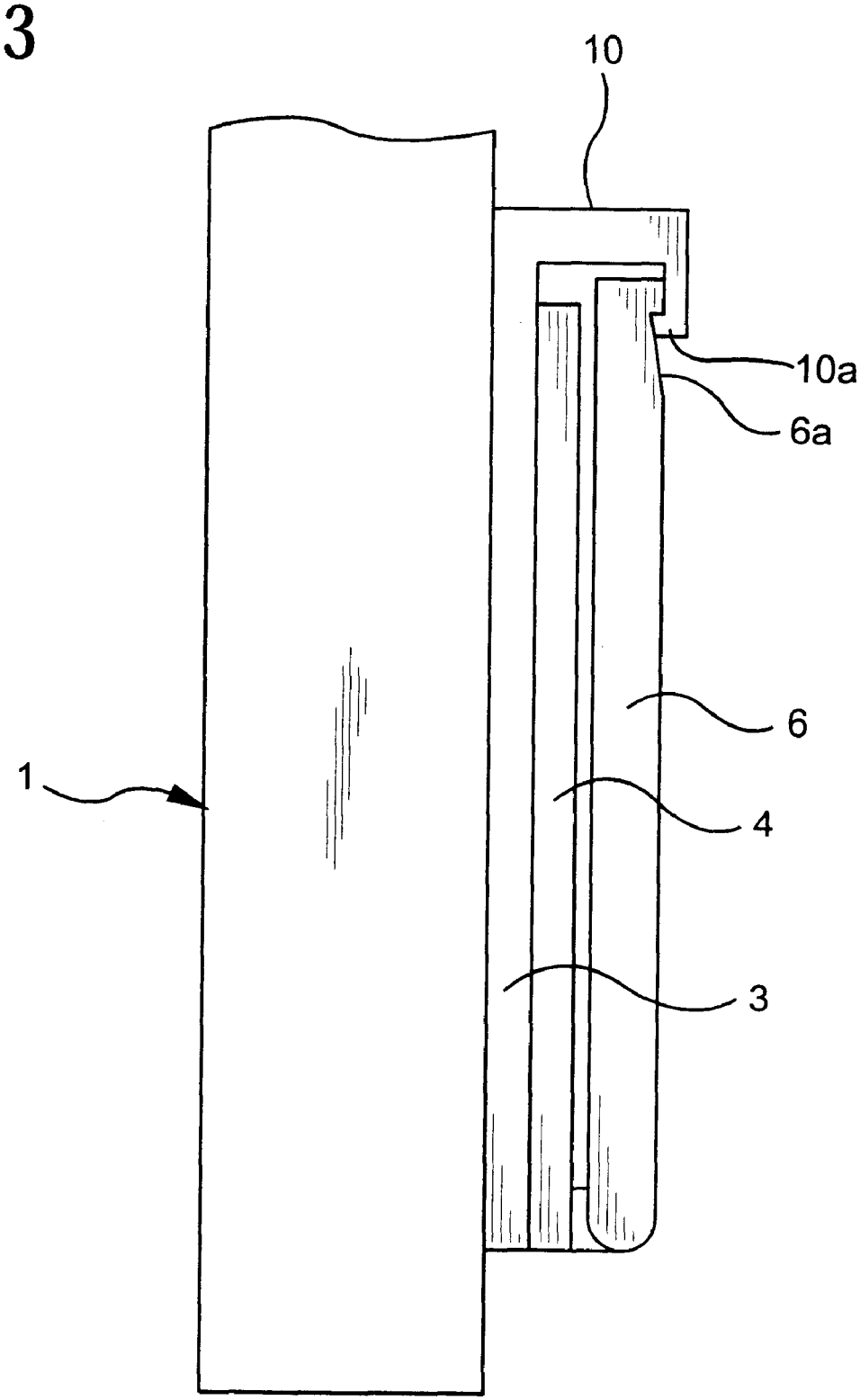
FIG. 3 is a diagram illustrating the storage state of the reference arm of the inclination angle detecting device shown in FIG. 1.

FIG. 3 shows the stored state of the slide plate 4 and the reference arm 6. A retaining portion 10 is provided to one end of the base plate 3. The retaining portion 10 has an L-shaped cross-section, wit the tip 10a thereof protruding inwards. This tip portion 10a engages with a recessed portion 6a provided to the rear of the reference arm 6, near the tip portion thereof.

Figure 4:
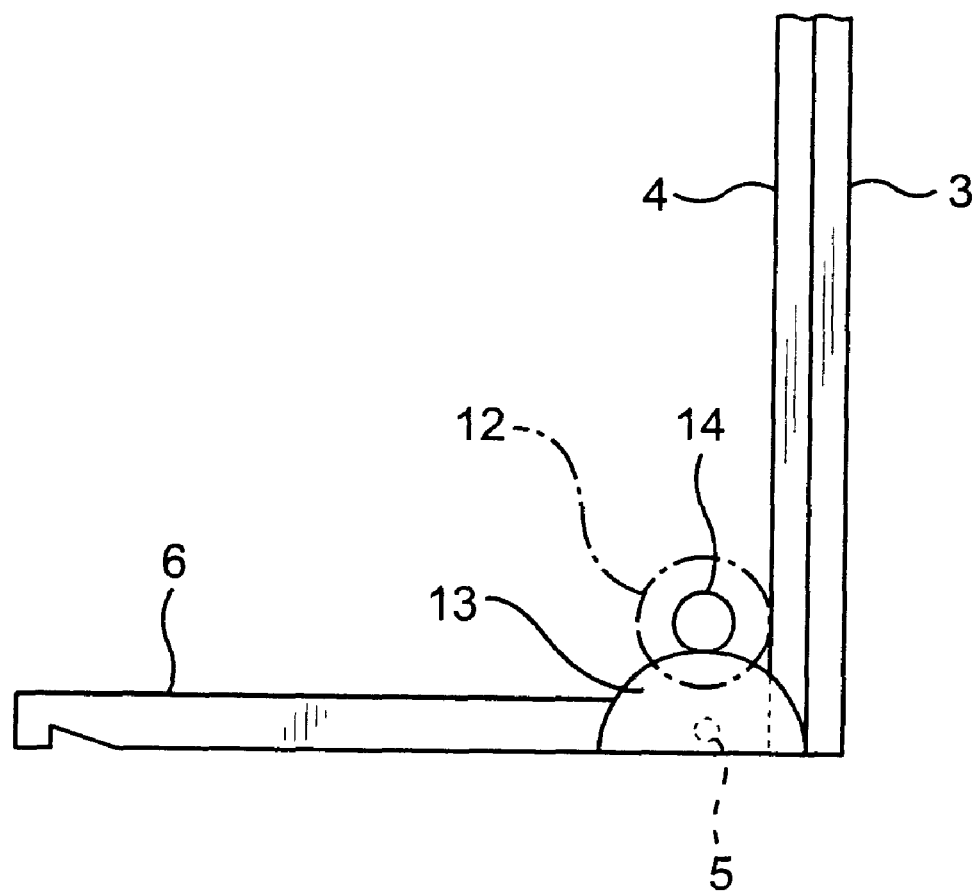
FIG. 4 is a diagram for describing the detecting unit of the inclination angle detecting device shown in FIG. 1.

Further, as shown in FIG. 1. the inclination angle detecting device 2 has an encoder 12 on a base plate 11 provided to the side plane 1b of the ultrasound probe 1, so as to serve as a detecting unit. As shown in FIG. 1 and FIG. 4, a half-disk-shaped gear 13 is attached to one end of the shaft 5 of the reference arm 6, and a gear 14 is attached to the rotating shaft of the encoder 12. The rotation of the shaft 5 of the reference arm 6 is transmitted to the encoder 12 via these gears 13 and 14. Accordingly, the encoder 12 detects the angle between the side 1b of the ultrasound probe 1 and the reference arm 6, i.e., the angle of the reference arm 6 as to the scanning plane A of the ultrasound probe 1. Incidentally, the lead line of the encoder 12 is connected with the cord portion 1c of the ultrasound probe 1 along with the lead line connected to the ultrasound transducers of the ultrasound probe 1, and externally extended.

Figure 5:
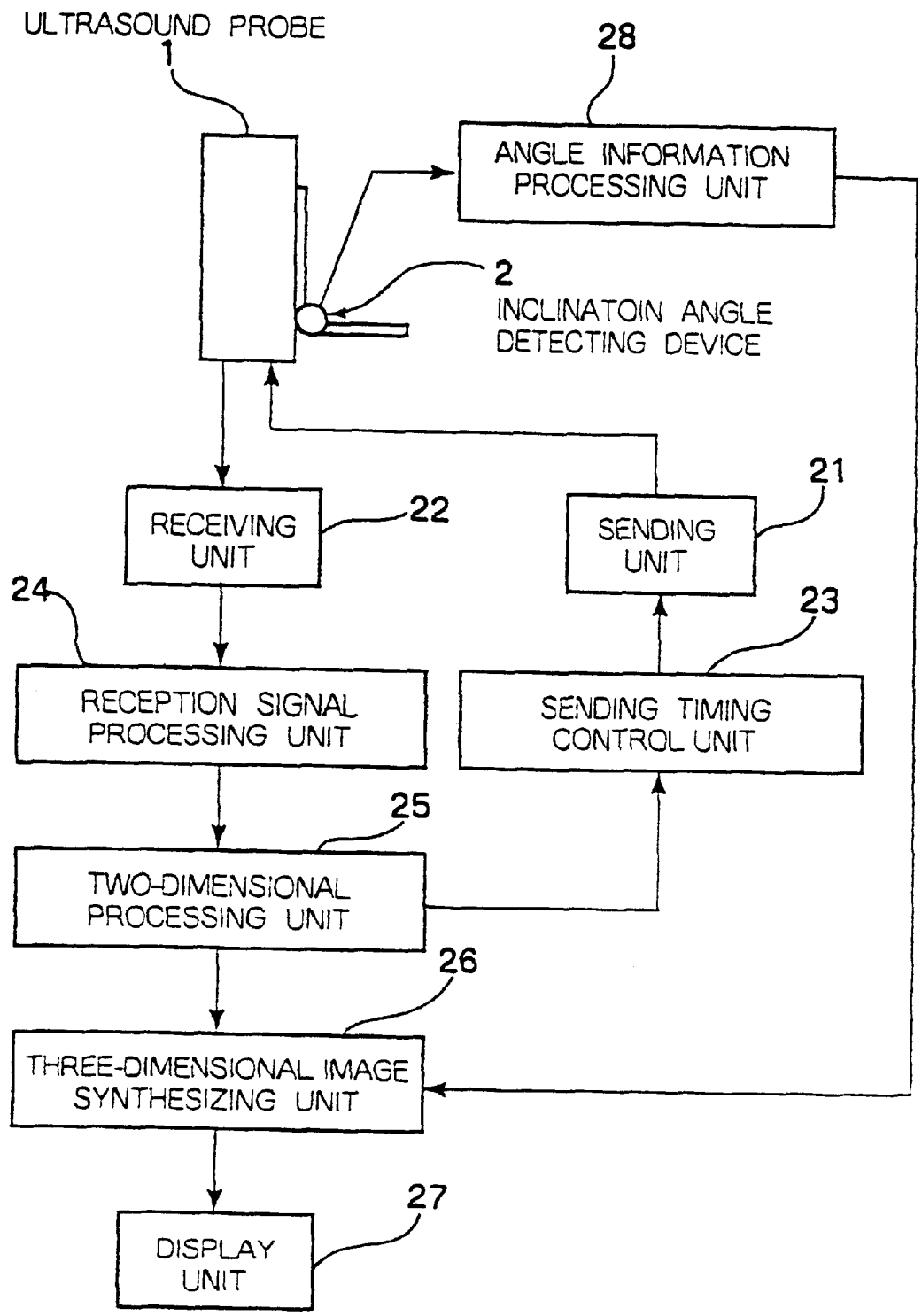
FIG. 5 is a diagram illustrating the overall configuration of a three-dimensional ultrasound apparatus using the probe shown in FIG. 1.

FIG. 5 shows the overall configuration of the three-dimensional uilrasound apparatus using this ultrasound probe 1. The inclination an 1e detecting device 2 is provided to the ultrasound probe 1. The ultrasound probe 1 is connected to a sending unit 21 for driving the ultrasound transducers and a receiving unit 22 for receiving the signals from the ultrasound transducers. A sending timing control unit 23 is connected to the sending unit 21 for controlling the timing of scanning with the ultrasound beams of the ultrasound transducers by controlling this sending unit 21, and a reception signal processing unit 24 is provided to the receiving unit 22 for signal processing of the signals received by the receiving unit 22, such as noise reduction, amplification, comparison. and so forth. A two-dimensional processing unit 25 is for controlling the sending timing control unit 23, and also creating a two-dimensional cross-section image based on the received signals obtained from the reception signal processing unit 24.

The angle information processing unit 28 is for detecting change in the angle detected by the inclination angle detecting device 2, in ceraint increments. A three-dimensional image synthesizing unit 26 is for taking the two-dimensional cross-section image from the two-dimnsional processing unit 25 and the detection signals from the angle information processing unit 28 and creating three-dimensional image information, and the display unit 27 is for displaying the image synthesized by the three-dimensional image synthesizing unit 26.

Next, the operation of an apparatus constructed thus will be described. First, the operator holds the ultrasound probe 1 in the stored state shown in FIG. 3, brings the contact area 1a which is the sending/receiving plane against the surface of the body of the subject at the position where measurement is to be performed, and once the area of interest has been determined. removes the reference arm 6 from the retaining portion 10. At this time, the cylindrical coil spring 8 presses the slide plate 4 so as to move toward the direction of the tip of the ultrasound probe 1. On the other hand, the torsion coil springs 9 press the reference arm 6 so that the angle with the slide plate 4 increases. Accordingly, the reference arm 6 comes into close contact with the surface of the body of the subject.

Figure 6A:
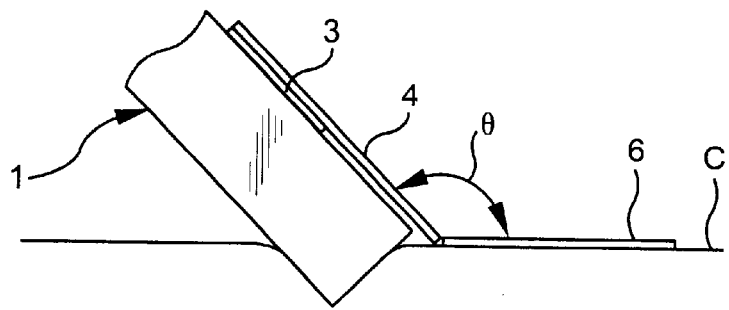
FIGS. 6A through 6C are diagrams each for describing the usage state of the probe shown in FIG. 1.
Figure 6B:
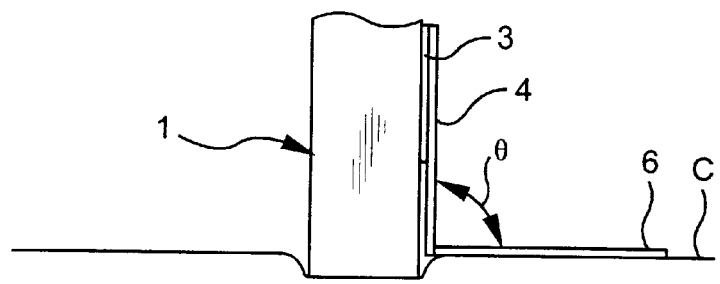
Figure 6C:
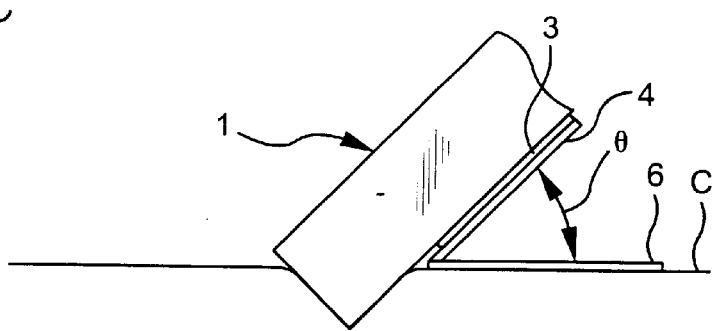

With the ultrasound probe 1 thus pressed against the surface of the body of the subject, the operator tilts the ultrasound probe 1 such that one side thereof draws nearer to the surface of the body of the subject, and then gradually erects the ultrasound probe 1 as to the surface of the body of the subject from the above state, following which the operator tilts the ultrasound probe 1 such that the other side thereof draws nearer to the surface of the body of the subject. At this time, the state of the ultrasound probe 1 on the surface of the body of the subject, and the slide plate 4 and reference arm 6 attached to the ultrasound probe 1 is as shown in FIGS. 6A–6C. FIG. 6A shows the ultrasound probe 1 being tilted in the direction opposite to the side to which the inclination angle detecting device 2 is provided. In this state, the tip of the slide plate 4 protrudes beyond the ultrasound probe 1, and the reference arm 6 is in close contact with the surface of the body C.

FIG. 6B shows the ultrasound probe 1 perpendicular to the surface of the body C. In this state, the tip of the slide plate 4 is near the contact area 1a of the ultrasound probe 1, and the reference arm 6 is in close contact with the surface of the body.

FIG. 6C shows the ultrasound probe 1 being tilted to the side to which the inclination angle detecting device 2 is provided. In this state. the tip of the slide plate 4 is retracted from the tip 1a of the ultrasound probe 1. and the reference arm 6 is in close contact with the surface of the body C.

Figure 7:
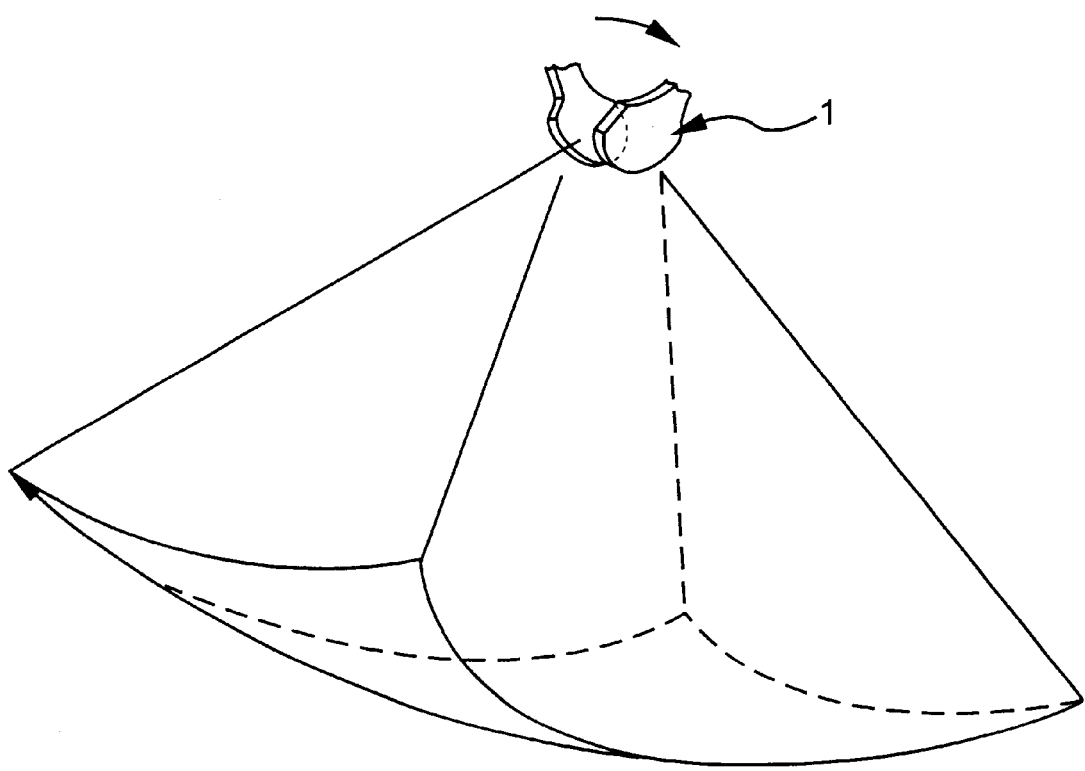
FIG. 7 is a diagram for describing the scanning state of the probe shown in FIG. 1.

In other words, in the event that the ultrasound probe 1 is pressed against the surface of the body C and is tilted in directions orthogonal to the scanning plane thereof. the reference arm 6 remains in close contact with the surface of the body C, however the ultrasound probe 1 may be tilted. Accordingly, the angle θ between the slide plate 4 and reference arm 6 is always the inclination angle of the ultrasound probe 1 as to the certain portion on the body surface C (the portion where the reference arm 6 is in close contact). FIG. 7 shows the state of scanning with the ultrasound probe 1.

Now, the encoder 12 detects the inclination angle of the ultrasound probe 1 as to the reference arm 6. and the angle information proceasing unit 28 outputs change in the detection angle of the encoder 12 in certain increments to the three-dimensional image synthesizing unit 26.

On the other hand, the sending unit 21 drives the ultrasound transducers under control of the sending timing control unit 23 so as to perform sending. The sent ultrasound beam reflects off of the object. of measurement, and returns to the ultrasound transducers. The receiving unit 22 receives the returning signals.

The signals which have returned to the receiving unit 22 are subjected to processing such as a noise reduction, amplification, comparison, etc., at the reception signal processing unit 24, thereby reaching the two-dimensional processing unit 25. The two-dimensional processing unit 25 creates a cross-sectional image from the reception signals provided thereto.

The three-dimensional image synthesizing unit 26 records cross-section images created by the two-dimensional processing unit 25 each time the ultrasound probe 1 tilts a certain angle based on the signals from the angle information processing unit 28, and once the three-dimensional image synthesizing unit 26 receives a certain number of cross-sectional images, creates a three-dimensional image based Thereupon, which is displayed on the display unit 27.

The inclination angle detecting device 2 according to the present apparatus has a slide plate 4, with a reference arm 6 attached to the tip thereof, so the reference arm 6 is in constant close contact with the object surface. Accordingly, the inclination angle of the ultrasound probe 1 can be precisely obtained whenever the operator presses the ultrasound probe 1 against the object surface and tilts it, without any special technique required. Accordingly, an even more precise three-dimensional image can be obtained.

In the above example, two-dimensional images created by the two-dimensional processing unit 25 may be directly displayed on the display unit 27, in the event that the reference arm 6 is in the stored state. Switching between two-dimensional display and three-dimensional display may be performed by a switched provided to the ultrasound probe 1 for example, or may be performed by a detecting device which detects whether or not the reference arm 6 is in the stored state.

What is claimed is:

1. An inclination angle detecting device for an ultrasound probe, said inclination angle detecting device comprising:
    a reference arm attached near a contact area of said ultrasound probe with a first end thereof being rotatably attached;
    a detecting unit attached to said ultrasound probe for detecting the inclination angle of said ultrasound probe as to said reference arm;
    a slide portion slidably provided along a side plane of said ultrasound probe;
    a pressing means which presses said slide portion in a direction toward the contact area of said ultrasound probe and beyond; and
    wherein said first end of said reference arm is rotatably attached at a tip of said slide portion.

2. An inclination angle detecting device for an ultrasound probe, said inclination angle detecting device comprising:
    a reference arm attached near a contact area of said ultrasound probe with a first end thereof being rotatably attached;
    a detecting unit attached to said ultrasound probe for detecting the inclination angle of said ultrasound probe as to said reference arm;
    a slide portion slidably provided along a side plane of said ultrasound probe;
    a pressing means which presses said slide portion in a direction toward the contact area of said ultrasound probe and beyond, said slide portion comprises a slide plate having a slit in the longitudinal direction through which a pair of pins erected on the side of said ultrasound probe are inserted, with a cylindrical coil spring being attached between said pin and the end of said slit in the longitudinal direction, so as to serve as said pressing means; and
    wherein said first end of said reference arm is rotatably attached to a tip of said slide plate and a second opposite end of said reference arm is free.

3. An inclination angle detecting device for an ultrasound probe, said inclination angle detecting device comprising:
    a reference arm attached near a contact area of said ultrasound probe with a first end thereof being rotatably attached;
    a detecting unit attached to said ultrasound probe for detecting the inclination angle of said ultrasound probe as to said reference arm;
    a slide portion slidably provided along a side plane of said ultrasound probe;
    a pressing means which presses said slide portion in a direction toward the contact area of said ultrasound probe and beyond;
    said slide portion comprises a slide plate having a slit in the longitudinal direction through which a pair of pins erected on the side of said ultrasound probe are inserted, with a cylindrical coil spring being attached between said pin and the end of said slit in the longitudinal direction, so as to serve as said pressing means and wherein said first end of said reference arm is rotatably attached to a tip of said slide plate by a shaft rotatably supported at the tip of said slide plate, and a second opposite end on said reference arm is free, and said detecting unit having a first gear attached to said shaft, said first gear meshing with a second gear attached to an encoder attached to the side plane of said ultrasound probe, so as to configure said detecting unit.

* * * * *